United States Patent [19]

Rice et al.

[11] Patent Number: 4,586,368
[45] Date of Patent: May 6, 1986

[54] ATMOSPHERIC PRESSURE HELIUM AFTERGLOW DISCHARGE DETECTOR FOR GAS CHROMATOGRAPHY

[75] Inventors: Gary Rice, Gloucester, Va.; Arthur P. D'Silva; Velmer A. Fassel, both of Ames, Iowa

[73] Assignee: The United States of America as represented by the United States Department of Energy, Washington, D.C.

[21] Appl. No.: 720,328

[22] Filed: Apr. 5, 1985

[51] Int. Cl.⁴ ............................................. G01N 30/74
[52] U.S. Cl. ..................................... 73/23.1; 356/311
[58] Field of Search .................... 73/23.1, 23; 324/464, 324/455; 356/311, 316

[56] References Cited

U.S. PATENT DOCUMENTS 4,309,187  1/1982  Dodge et al. ........................ 356/316
4,509,855  4/1985  Gay ..................................... 356/316
4,532,219  7/1985  Hagen et al. ........................ 356/316

OTHER PUBLICATIONS

A. Karmen et al., "A Radio Frequency Glow Detector for Gas Chromatography," *Annals of New York Acad. of Sciences*, vol. 72, Art No. 13, pp. 714–719, Mar. 1959.

Primary Examiner—Stephen A. Kreitman
Attorney, Agent, or Firm—James W. Weinberger; Arthur A. Churm; Judson R. Hightower

[57] ABSTRACT

An apparatus for providing a simple, low-frequency electrodeless discharge system for atmospheric pressure afterglow generation. A single quartz tube through which a gas mixture is passed is extended beyond a concentric electrode positioned thereabout. A grounding rod is placed directly above the tube outlet to permit optical viewing of the discharge between the electrodes.

7 Claims, 2 Drawing Figures

ATMOSPHERIC PRESSURE HELIUM AFTERGLOW DISCHARGE DETECTOR FOR GAS CHROMATOGRAPHY

CONTRACTUAL ORIGIN OF THE INVENTION

The United States Government has rights in this invention pursuant to Contract No. W-7405-ENG-82 between the U.S. Department of Energy and Iowa State University.

BACKGROUND OF THE INVENTION

In a gas chromatography system, a carrier gas such as helium, hydrogen or nitrogen is usually passed through a chromatograph i.e., a specially treated glass or silica column contained in an oven. An injection device is located near the inlet to the column so that samples, such as gases or volatile liquids, may be introduced into the carrier gas stream. Generally, the injection port is heated so that liquid samples are quickly vaporized. Such samples, a few microliters of liquid or a few milliliters of gas, are commonly introduced through a rubber septum by means of a hypodermic syringe.

The chromatograph column is contained in an oven, which can either be maintained at a constant temperature or can be programmed to increase in a stepwise fashion. As the carrier gas stream passes through the column, it will partition and desorb the compounds on the column. The partitioning factor depends on the column material and the temperature at which the column is maintained. The carrier gas containing the compounds then exits into a detector, which is one of the key elements of gas chromatographic instrumentation. Commercial detectors can be non-selective or partially selective. Partially selective detectors only detect certain types of compounds, while non-selective detectors will detect all types of compounds, but cannot distinguish between certain atoms, such the halogens, phosphorous, sulfur or nitrogen.

Microwave induced plasmas are element selective multielement detectors which utilize helium or argon as the support gas. However, there are some problems associated with these detectors, for example the device requires large volumes of the support gas, having flow rates of about 1 to 4 liters per minute. The decomposition of organic compounds results in the deposition of carbon on the inner wall of the discharge tube requiring frequent clean-up. The injection of large quantities of sample or solvent can quench the plasma requiring a complete restart. The observation zone in the discharge varies widely for obtaining optimum limits of detection. The optimum flow rates for the optimum limits of detection also vary widely.

Element selective multielemental gas chromatography detectors utilizing atmospheric pressure afterglows generated from nitrogen or argon as excitation sources have been developed. During this development, it has been found that the production of these afterglows from electrodeless, ozonizer-type discharge tubes has provided an attractive solution for this purpose. In particular, the production of such afterglows from a simple, low-frequency, electrodeless discharge system has been found to be especially suitable.

However, these afterglows were found to have some limitations. For example, in the case of nitrogen, element-selective detection was restricted to atomic emission from metal containing eluents and from carbon, through the formation of CN emission from eluting organic compounds. Only molecular emission from PN, $S_2$, NCl and NBr has been observed when P, S, Cl and Br containing compounds have been injected into a nitrogen afterglow. In an argon afterglow, the atomic spectra of Cl and Br are detectable, however, the measured detection limits are marginal for gas chromatography applications.

An atmospheric pressure afterglow method and apparatus utilizing helium has been developed which is capable of element-selective detection, and has excellent limits of detection and linear ranges. The apparatus provides a high level of reproducibility with between 5 to 10 percent deviation. No deleterious post-solvent effects have been observed on the tube or in the discharge such as occurs with other detectors resulting in deposit formation on the tube or extinguishment of the discharge, respectively. The invention utilizes a low rate of helium consumption, and is simple in construction and maintenance. The construction also eliminates the problems that can occur due to dead volume between the gas chromatography column and the detector which occur in other types of systems such as microwave induced plasmas, resulting in poor resolution of the compounds being eluted from the column.

SUMMARY OF THE INVENTION

In order to provide such atmospheric pressure afterglows, it is an object of the present invention to produce such afterglows from electrodeless, discharge tubes.

Another object of the invention is the provision of a simple, electrodeless discharge system for atmospheric pressure afterglow generation using helium.

Another object of the invention is the provision of an apparatus of the type set forth which is characterized by an easily sustained discharge at low-flow rates of helium with a relatively clean emission background.

These and other objects of the invention are attained by providing a simple, low-frequency, electrodeless discharge system which, in a preferred embodiment, utilizes a single discharge tube which penetrates and extends above a cylindrical stainless steel electrode. A stainless steel rod placed directly above the tube outlet serves as a grounding rod, while the volume between the two electrodes forms the afterglow region. A sample tube extends axially through the discharge tube to a point just above the top of the cylindrical electrode to deliver the sample directly into the afterglow region. Optical viewing of the afterglow is then effected between the electrodes. The afterglow is easily sustained at flow rates of helium as low as 40–50 milliliters per minute at incident power of between 40 to 250 watts.

Additional objects, advantages, and novel features of the invention will be set forth in part in the description which follows, and in part will become apparent to those skilled in the art upon examination of the following, or may be learned by practice of the invention. The objects and advantages of the invention may be realized and attained by means of the instrumentalities and combinations particlarly pointed out in the appended claims.

DESCRIPTION OF THE FIGURES

For the purpose of facilitating an understanding of the invention, there is illustrated in the accompanying drawings a preferred embodiment thereof, from an inspection of which, when considered in connection with the following description, the invention, its construction and operation, and many of its advantages should be readily understood and appreciated.

DETAILED DESCRIPTION OF THE INVENTION

Figure 1:
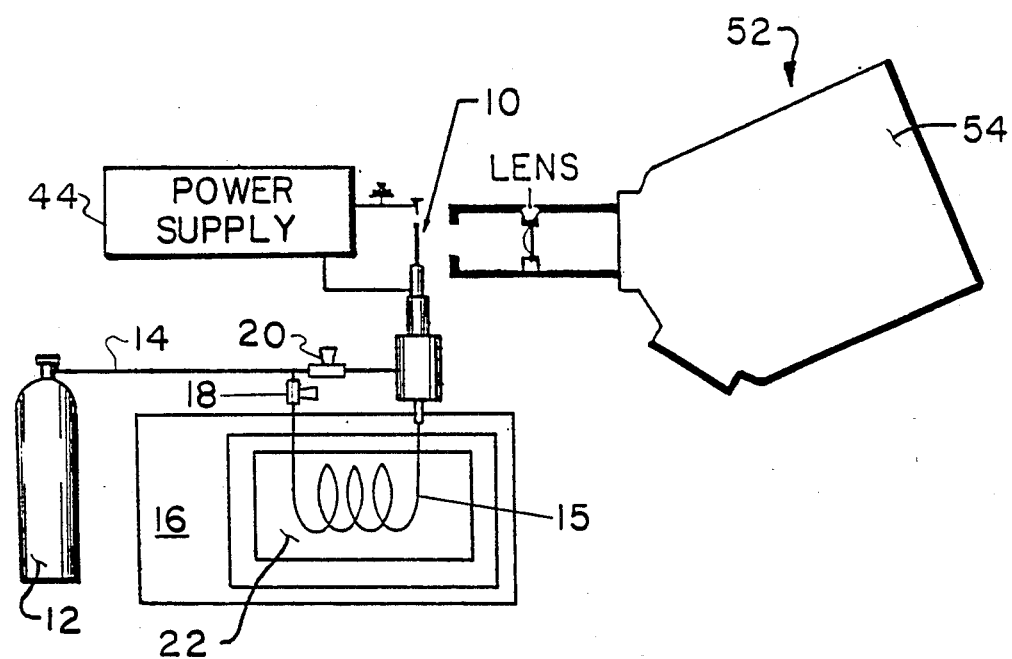
FIG. 1 is a schematic diagram of a gas chromatography apparatus utilizing the present invention.

Referring to FIG. 1, there is illustrated a gas chromatography system which includes an electrodeless afterglow discharge system 10 constructed in accordance with and embodying the features of the present invention. As briefly discussed above, the gas chromatography system includes a source 12 of a carrier gas, such as helium, supplied through a line 14 to a capillary tube 15 in gas chromatograph 22 through a metering valve 18. Line 14 also connects with a second metering valve 20 to control the flow of helium to discharge system 10, which will be discussed below. Valve 18 controls the introduction of the carrier gas to control the flow at the inlet to the gas chromatograph which, as previously discussed, is maintained at a constant temperature or heated in a stepwise fashion in oven 16.

Figure 2:
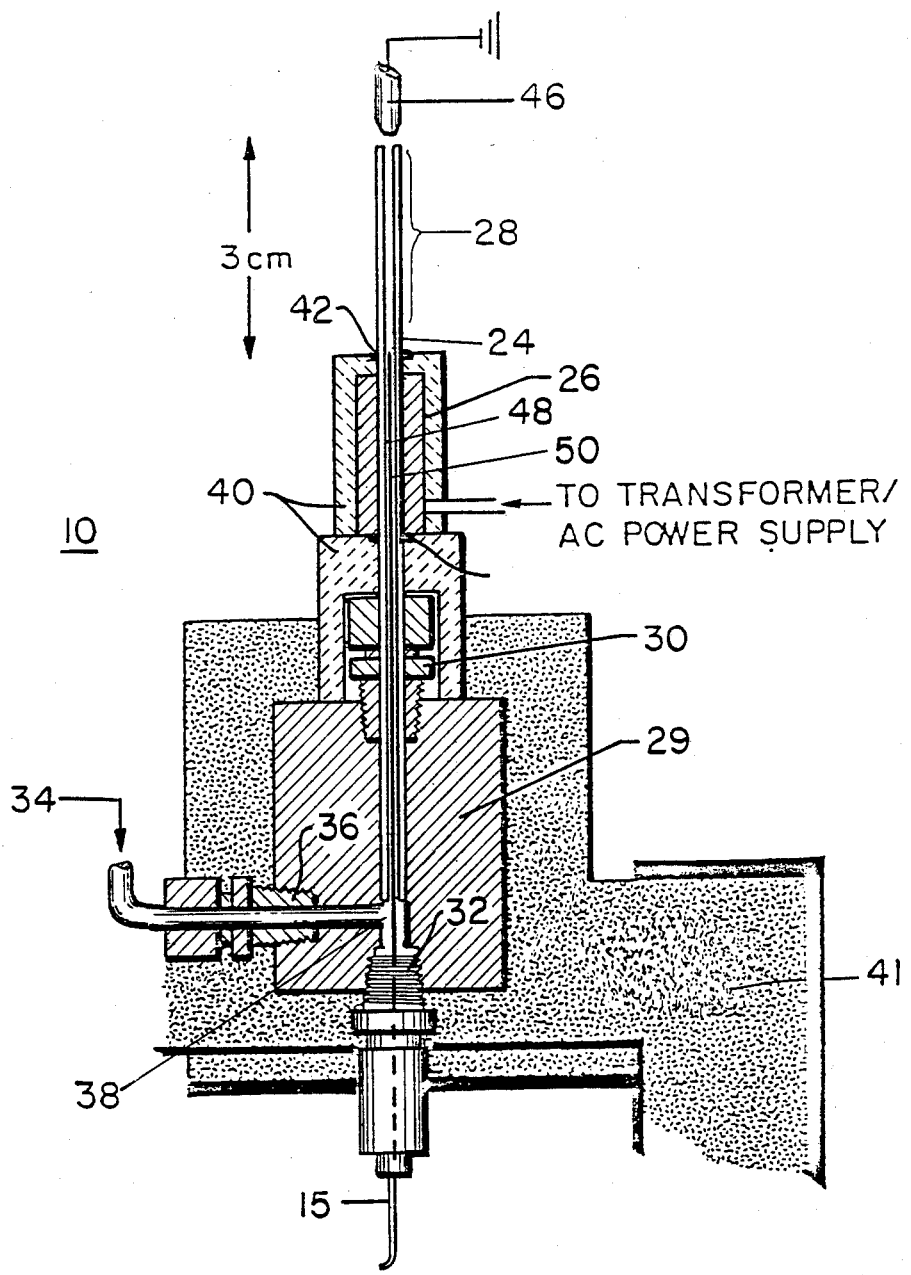
FIG. 2 is an enlarged view in vertical section of a portion of the gas chromatography apparatus to better illustrate the instant invention.

Referring now to FIG. 2, a single quartz or sapphire discharge tube 24, preferably about 3 mm o.d. by 1 mm i.d. extends axially through an approximately 2 cm long cylindrical stainless steel electrode 26 to a point about 3 cm above the top of electrode 26 to form the afterglow region 28 of the system. Tube 24 is supported in a heater block 29 by upper and lower Swagelock fittings 30 and 32 respectively. Metering valve 20 controls a flow of helium through line 34 passing through a fitting 36 in heater block 29 to a T-connection 38 with discharge tube 24.

Suitable ceramic insulators 40 are positioned about the stainless steel electrode 26, with O-ring seals 42 interposed therebetween. Thermal insulation 41 encloses heater block 29. Electrode 26 is coupled to a suitable power supply 44 (as shown in FIG. 1) to couple the electrode 26 to the power source, which may vary in frequency from about 26 to 300 KHz while insulating the electrode from the surrounding area. A suitably grounded stainless steel grounding rod 46 is placed directly above the outlet of the discharge tube 24, and serves as the grounding electrode.

A sample tube 48, is positioned axially within discharge tube 24 forming an annular space 50 within the tube. Tube 48 extends from lower fitting 32 to an area between the top of electrode 26 and the top of insulation 40 in order to discharge the sample directly into the afterglow region. Tube 48 may be either a separate tube set in fitting 32 to which capillary tube 15 is connected or capillary tube 15 may be threaded through fitting 32 and into discharge tube 24 to the proper position just below the afterglow region.

A spectrometric analysis system 52 is positioned with a monochromator 54 in optical alignment with the afterglow region 28 of the electrodeless discharge system 10 to detect and record the desired data.

In operation, a flow of helium from tank 12 is controlled by valve 20 at a rate of about 80 ml per minute into annular space 50. Heater 29 is set at a temperature of about 400° C. to prevent any condensation of sample from the gas chromatograph. A power of about 45 watts at from 26 to 27 KHz is initiated in electrode 26. Initiation of the He discharge results in a blue emission in both the discharge and afterglow regions due to residual nitrogen collected on the surface of the gas lines. No external means for startup is required. After 10 to 15 minutes, the discharge and afterglow become pink in color due to neon in the He gas stream.

Once the afterglow has been established, it is a simple matter for introduction of the sample into the afterglow.

While the apparatus of the invention is operable without the presence of grounding electrode 46, the electrode is preferred because it provides an enhanced uniform intensity between the electrodes throughout the entire 3 cm length of the afterglow region.

The frequency of the power supply may vary for about 26 to about 300 KHz at a power of 40 to 200 watts at 2 to 20 KV. For example, good results have been obtained at 26 KHz at about 45 watts at 15–20 KV and at 200 KHz at about 50 watts at 2 KV.

Helium flow rates may vary from about 40–100 ml/min and are based on the optimum spectral line intensity of the elements being detected.

The apparatus of the invention should be able to detect all elements but helium.

The following operating conditions of a preferred system have been found to be as follows:

| OPERATING CONDITIONS | | |
|---|---|---|
| (A) | Discharge System | |
| | He Flow Rate: | 80 cc/min |
| | Incident Power: | 45 watts (ENI Power Systems) |
| | Frequency:* | 26–27 KHz at 15 to 20 KV |
| (B) | Spectrometric System | |
| | Monochromator: | 0.3 m (McPherson) or equivalent |
| | Bandpass (FWHM) | 0.2 nm |
| | PMT/180–300 nm: | EMI Solar Bind (1850V) |
| | 300–900 nm: | RCA ER60 (1500V) |
| (C) | Chromatographic System | |
| | Gas Chromatograph: | Hewlett-Packard Model 5710A capillary GC |
| | Carrier Gas: | Helium |
| | Column: | Durabond 5 (J & W); 30 meter |

*The voltage can change if a power supply operating at a higher frequency (~200 KV) is available.

Various test compounds were utilized to detect different elements, and the test compounds for those particular elements are listed in Table I setting forth the particular element to be detected, the test compound utilized for the detection, the analytical wave length, absolute limit of detection, linear range and selectively ratio.

TABLE I

| Element | Analytical Wavelength (nm) | Absolute Limits of Detection (pg) | Linear Range | Selectivity Ratio | Test Compound |
|---|---|---|---|---|---|
| F | 739.9 | 20 | $1 \times 10^4$ | $5 \times 10^3$ | Fluorobenzene |
| Cl | 837.6 | 8 | $5 \times 10^4$ | $1 \times 10^4$ | trichloroethane |
| Br | 827.2 | 15 | $1 \times 10^4$ | 100 | dibromomethane |
| I | 183.0 | 2 | $2 \times 10^4$ | 200 | 2-iodopropane |
| C | 193.1 | 10 | $5 \times 10^2$ | | octane |
| P | 213.6 | 30 | $1 \times 10^3$ | 80 | trimethylphosphite |
| S | 182.0 | 5 | $1 \times 10^3$ | 60 | thiophene |
| Si | 251.6 | 50 | $5 \times 10^2$ | 40 | triethoxyethylsilane |
| Hg | 253.6 | 0.5 | $1 \times 10^5$ | $7 \times 10^3$ | diethylmercury |
| As | 189.0 | 20 | $5 \times 10^2$ | 20 | triphenylarsine |

In general, limits of detection for all the elements thus far have been 50 pg or less, with linear response to concentration from two to three orders in magnitude. Selectivities have been observed to be poorer for elements with analytical wave lengths in the UV region, a factor believed attributable to the formation of CO emission, which can be corrected by appropriate instrumentation.

The apparatus of the invention has significant advantages over prior art devices. For example, effluents are introduced above the primary discharge region. Although temporary quenching of the afterglow region does occur from excessive solvent loading, the afterglow is continuously replenished from the primary discharge. Thus, the stability of the afterglow is maintained. The device is relatively easy to construct and He gas consumption is low when compared with other devices of a similar nature.

From the preceding discussion, it can be seen that the apparatus of the invention is a suitable and effective element selective multielemental detector for use with a gas chromatograph.

The embodiment of the invention in which an exclusive property or privilege is claimed is defined as follows:

1. An electrodeless discharge apparatus for use in producing atmospheric pressure afterglows from helium as an element specific, multielemental gas chromatography detector comprising: a discharge tube having an upper open end, and a lower end means for supplying helium at atmospheric pressure to the discharge tube, a first electrode concentrically encircling at least a portion of said tube near the upper end and coupled to a suitable high frequency power source for applying power at a predetermined frequency to excite the helium, a second grounded electrode positioned coaxially with the upper open end of the tube, but spaced therefrom, for creating an afterglow region in the tube between the two electrodes and, sample discharge means for depositing a sample from the gas chromatograph into the afterglow region.

2. The apparatus of claim 1 wherein the discharge tube is a quartz tube which extends approximately 3 cm above the first electrode.

3. The apparatus of claim 2 wherein the electrode power source has a frequency from about 26 to 200 KHz.

4. The apparatus of claim 3 wherein the lower end of the discharge tube is provided with heating means to prevent condensation of the sample.

5. The apparatus of claim 4 wherein the flow rate of helium is from 40 to 100 ml/min.

6. The apparatus of claim 5 wherein the sample discharge means is a sample tube having a top and a bottom ends positioned axially within the discharge tube, the top of the sample tube being positioned just above the first electrode, the sample tube forming an annular space within the discharge tube to supply helium to the afterglow region, the bottom of the sample tube being connected to a capillary tube from the gas chromatograph.

7. The apparatus of claim 5 wherein the sample discharge means is a capillary tube from a gas chromatograph positioned axially within the discharge tube, to form an annular within the discharge tube to supply helium to the afterglow region, the capillary tube having a top end positioned just above the top of the first electrode.

* * * * *